(12) United States Patent
Rastrelli et al.

(10) Patent No.: US 6,897,203 B2
(45) Date of Patent: May 24, 2005

(54) POLYSACCHARIDIC ESTERS OF RETINOIC ACID

(75) Inventors: Alessandro Rastrelli, Padua (IT); Giuliana Miglierini, Varese (IT); Alberto Perbellini, Verona (IT); Luca Stucchi, Pavia di Udine (IT)

(73) Assignee: Eurand Pharmaceuticals Ltd. (IE)

( * ) Notice: Subject to any disclaimer, the term of this patent is extended or adjusted under 35 U.S.C. 154(b) by 0 days.

(21) Appl. No.: 10/483,638

(22) PCT Filed: Jan. 16, 2002

(86) PCT No.: PCT/EP02/07895

§ 371 (c)(1),
(2), (4) Date: Jan. 14, 2004

(87) PCT Pub. No.: WO03/008457

PCT Pub. Date: Jan. 30, 2003

(65) Prior Publication Data

US 2004/0171581 A1 Sep. 2, 2004

(30) Foreign Application Priority Data

Jul. 17, 2001 (IT) ...................................... TS2001A0017

(51) Int. Cl.$^7$ ...................... A61K 31/715; A61K 31/203

(52) U.S. Cl. .......................... 514/54; 514/559; 514/560; 536/123.1

(58) Field of Search .......................... 514/54, 559, 560; 536/123.1

(56) References Cited

U.S. PATENT DOCUMENTS

| | | |
|---|---|---|
| 4,371,673 A | 2/1983 | Pitha |
| 4,933,440 A * | 6/1990 | Dussourd d'Hinterland et al. ............................ 536/53 |
| 6,140,313 A | 10/2000 | Perbellini et al. |
| 6,482,941 B1 | 11/2002 | Khan Riaz et al. |

FOREIGN PATENT DOCUMENTS

| | | |
|---|---|---|
| WO | 98/23648 | 6/1998 |
| WO | 99/18133 | 4/1999 |

OTHER PUBLICATIONS

C. Ventura et al., "Phorbol Ester Regulation of Opioid Peptide Gene Expression in Myocardial Cells," *The Journal of Biological Chemistry*, vol. 270, No. 50, pp. 30115–30120 (Dec. 1995).

M. W. McBurney et al., "Control of muscle and neuronal differentiation in a cultured embryonal carcinoma cell line," *Nature*, vol. 299, pp. 165–167 (Sept. 1982).

P. Chomczynski et al., "Single–Step Method of RNA Isolation by Acid Guanidinium Thiocyanate–Phenol–Chloroform Extraction," *Analytical Biochemistry*, 162, pp. 156–159 (1987).

C. Ventura et al., "Opioid Peptide Gene Expression Primes Cardiogenesis in Embryonal Pluripotent Stem Cells," *Circulation Research*, pp. 189–194 (Aug. 2000).

I.S. Skerjanc et al., "Myocyte Enhancer Factor 2C and Nkx2–5 Up–regulate Each Other's Expression and Initiate Cardiomyogenesis in P19 Cells," *The Journal of Biological Chemistry*, vol. 273, No. 52, pp. 34904–34910 (Dec. 1998).

C. Grépin et al., "Inhibition of Transcription Factor GATA–4 Expression Blocks in Vitro Cardiac Muscle Differentiation," *Molecular and Cellular Biology*, vol. 15, No. 8, pp. 4095–4102 (Aug. 1995).

* cited by examiner

*Primary Examiner*—James O. Wilson
*Assistant Examiner*—Michael C. Henry
(74) *Attorney, Agent, or Firm*—Thompson Hine LLP

(57) ABSTRACT

The present invention relates to polysaccharidic esters of retinoic acid, wherein the hydroxyl groups of the monosaccharidic units of the polysaccharide are partially or totally esterified with retinoic acid. A process to obtain these esters is also described. The products according to the present invention can be used in the pharmaceutical and cosmetic field.

19 Claims, No Drawings

POLYSACCHARIDIC ESTERS OF RETINOIC ACID

FIELD OF THE INVENTION

The present invention sets in the field of polysaccharidic esters of retinoic acid. The invention includes the process for their preparation. The compounds can be used in the pharmaceutical and cosmetic field.

STATE OF THE ART

Several modified polysaccharides have been described in the state-of-the-art. They have been obtained by chemical modification of the groups present onto the polysaccharidic chain, such as for example hydroxyl groups, carboxyl groups, amino groups, which results in the formation, for example, of new ester and amide derivatives. The possibilities of application are several and cover several industrial branches, like food, varnishes, chemo-analytical ones, cosmetics, and pharmaceutics. In the pharmaceutical area, polysaccharides are regarded as compounds suitable for the preparation of pharmaceutical compositions, biomaterials, and drug controlled release systems. They are, in fact, extremely well tolerated by the organism since several polysaccharides and their oligomers play important biological roles therein. When polysaccharides are used for the preparation of controlled release systems of pharmacologically active molecules, they can be either present in a mixture with said molecules or be covalently bound to them by means, for example, of ester or amide linkages.

Besides their function as carriers, some polysaccharides have their own biological activity and some can be components of the organism: for example, heparins, are anticlotting agents; hyaluronan is the main component of the vitreous body and of the synovial fluid; they are moreover used in clinic for the treatment of osteoarthrosis and artropathies. Another polysaccharide, scleroglucan is used in the treatment of some tumours or in combination with other drugs in immunostimulating treatments. Several sulphated polysaccharides of bacterial origin are effective in the treatment of rheumatoid arthritis, retinopathy, and psoriasis. Moreover, some polysaccharides have the ability of recognising cellular receptors. This makes their use very interesting when a drug release to specific sites is necessary or desirable.

DETAILED DESCRIPTION OF THE INVENTION

The object of this invention is a new class of polysaccharidic esters of retinoic acid, wherein the hydroxyl groups of the monosaccharidic units of the polysaccharide are either partially or totally esterified with retinoic acid.

The esterification process between retinoic acid and the polysaccharide occurs between the carboxyl group of retinoic acid and the hydroxyl groups of the monosaccharidic units of the polysaccharide. This can involve either the primary hydroxyl groups or the secondary hydroxyl groups or both the primary and secondary hydroxyl groups.

The degree of esterification of these polysaccharidic esters ranges from $1 \times 10^{-6}$ to $3 \times 10^{-1}$, most preferably from 0.2 to 0.02. The term "degree of esterification (DE)" indicates the number of moles of retinoic acid per polysaccharidic moles. Retinoic acid, i.e. 3,7-dimethyl-9-(2,6,6-trimethyl-1-cyclohexene-1-yl)-2,4,6,8-nonatetraenoic acid in its natural form, shows all the double bonds in trans-form (all-trans). The term "retinoic acid" used in the present invention includes all the possible isomeric forms, hence besides the trans-isomer also the other possible cis-trans forms are included. The preferred forms for the preparation of the compounds of the invention are the all-trans-retinoic-acid and the 13-cis-7,9,11-tri-trans-retinoic acid. Retinoic acid and more generally retinoids play fundamental biological functions in the organism; specifically its role is important in the vision, embrional growth, and in the maintenance of a normal and healthy skin state.

The polysaccharide used for the preparation of esters according to the present invention is a polysaccharide from natural source. Polysaccharides can be isolated from natural sources such as, for example, animal sources, among which man, plants, and microorganisms. They have preferably a weight average molecular weight (MW, determination by High Performance Size Exclusion Chromatography and/or coupled with a molecular size detector, for example light scattering) ranging from 8000 to 3000000. In order to obtain the derivatives that are the object of this invention, the polysaccharides having a weight average molecular weight ranging from 30000 to 1500000 are preferred. Polysaccharides can have either a linear or branched structure. The polysaccharide is said to be branched when its polysaccharidic backbone contains side chains constituted of one or more monosaccharidic or oligosaccharidic units. Polysaccharides are constituted of monosaccharidic units such as D-glucose, D-xylose, D-arabinose, D- and L-mannose, D-galactose, L-fucose, D-fructose, L-rhamnose, D-glucuronic acid, D-mannuronic acid, L-guluronic acid, L-iduronic acid, D-galacturonic acid, N-acetyl-D-glucosamine, 3,6-anhydro-D-galactose, N-acetyl-D-galactosamine, 3,6-anhydro-L-galactose, 2-amino-2-deoxy-D-glucose. Besides, these monosaccharides can optionally contain further substituents such as sulphated or acetyl or succinyl groups. In the polysaccharidic backbone, the monosaccharidic units are linked by $\beta$-(1→3), $\beta$-(1→2), $\beta$-(1→4), $\alpha$-(1→3), $\alpha$-(1→4), $\alpha$-(1→6) bond $\beta$-configuration is the preferred one. The side chains are preferably constituted of monosaccharidic units linked by $\beta$-(1→2), $\beta$-(1→3), $\beta$-(1→4), $\beta$-(1→6), $\beta$-(1→4), $\beta$-( bonds, even more preferably by $\beta$-(1→6).

When the polysaccharide is neutral, it is preferably selected in the group consisting of glucans (glucose polysaccharides) isolated from fungi, plants, algae, bacteria, yeasts. Said polysaccharides can be either linear or branched. The preferred (1→3)-$\beta$-D-glucans (hereinafter $\beta$-D-glucans) are polysaccharides composed of residues of (1→3)-$\beta$-D-glucose. Preferred examples are: scleroglucan, lentinan, schizophyllan, pachimaran, laminaran and curdlan.

Among the anionic polysaccharides, the carboxylated polysaccharides or their salts, such as hyaluronan (also called hyaluronic acid), can be advantageously used. Hyaluronan is composed of this repeating unit: (1→3)-$\beta$-N-acetyl-D-glucosamine-(1→4)-$\beta$-D-glucuronic acid.

The relevant anionic polysaccharides for the preparation of the esters of this invention can be salified with cations of alkaline or earth alkaline metals, preferably the C1–C5 alkylammonium cations. Said carboxylated polysaccharides can also be used in the forms where the carboxyl groups are esterified with alcohols of the aliphatic, alkylaliphatic, cycloaliphatic, heterocyclic series.

Another class of anionic polysaccharides is that of the sulphated polysaccharides, such as, for example, heparins or chrondroitin sulphate or dermatan sulphate.

Other natural sulphated polysaccharides that are interesting to obtain the products according to the present invention belong to the class of polysaccharides than can be isolated from a marine alga, such as *Grateloupia doryphora* or *G. filicina*, of the *Grateloupiaceae* family, described in WO98/23648. It is possible to use also other sulphated polysaccharides that can be isolated from other algae of the *Grateloupiaceae* or *Codiaceae* families or from microorganisms.

Finally, it is possible to use also either neutral or anionic natural polysaccharides derivatized with molecules containing groups salified with sulphated, phosphated or carboxylated groups.

When the hydroxyl groups of the monosaccharidic units of the polysaccharide are partially esterified with retinoic acid, the free hydroxyl groups of the monosaccharidic units that are not involved in the ester bond with the retinoic acid can be further substituted by means of esterification with acids having C1–C5-alkyl chain. The preferred acids are the carboxylic acids having C1–C6 carbon atoms, such as for example acetic acid, propionic acid, and butanoic acid. Among these, butanoic acid is the preferred one.

One further aspect of the invention is the preparation process of the esters of the invention.

The process allows the formation of the ester bond between the acid group (carboxylic group) of the retinoic acid and the hydroxyl groups of the monosaccharidic units of the polysaccharide. The reaction can take place either on the acid group as such or on one of its reactive forms; it can also take place on the hydroxyl groups as such or on one of their activated forms.

When retinoic acid is used in a reactive form, one possible preparation can be obtained by activating the acid group with the formation of anhydrides, esters (with alcohols that can be leaving groups, such as for example $CF_3CH_2O$) acyl halides (with, for example, chloridric acid, N-halosuccinamide, tri- or penta-phosphorous halide).

One of the preferred embodiments of the present invention entails the preparation of the acyl halide of retinoic acid that is carried out by halogenation of retinoic acid in the presence of an halogenating agent, for example oxalyl halide, in the presence of an organic solvent or mixtures of organic solvents, at room temperature and for a time span ranging from 5 to 30 minutes. The preferred solvents are N,N-dimethylformamide, N,N-dimethylacetamide, N-methylpyrrolidone, possibly in a mixture with other solvents such as for example ethyl ether.

One further reactive form of retinoic acid is represented by an adduct between retinoic acid and a condensing agent that is obtained by mixing retinoic acid in an organic solvent, for example dimethylsulphoxide, N-methylpyrrolidone, N-methylformamide with a condensing agent selected in the group consisting of dicyclohexylcarbodiimide, N-methyl-2-halo-pyridinium halide, 2-halo-pyridinium halide.

When the esterification reaction occurs on the hydroxyl groups of the monosaccharidic units of the polysaccharide in their activated forms, the activation can be either selective or non-selective. The selective activation involves exclusively the primary hydroxyl groups of the monosaccharidic units or exclusively the secondary ones, while the non selective one involves at the same time both the primary and the secondary hydroxyl groups.

The non-selective activation of the hydroxyl groups of the monosaccharidic units of the polysaccharide is a procedure that makes said groups more reactive. It can be obtained by replacing the hydroxyl groups with leaving groups, which can be obtained for example by reacting the polysaccharide with trifluorosulphonic acid, metansulphonic acid, p-toluensulphonic acid, derivatives of formic acid or carbonic acid. As an alternative, the activation can be carried out by the formation of salts, alcoholates, that increase the nucleophilicity of the hydroxyl group.

In one of the preferred embodiments of the invention, the activation is carried out through the formation of alcoholates. The polysaccharide activated in this way is suspended in a suitable organic solvent or in a mixture of organic solvents, wherein said organic solvent is selected preferably in the group consisting of N,N-dimethylformamide, dimethylsulphoxide, N-methylpyrrolidone. It is kept under constant stirring for some hours (1–5 hours) before performing the esterification reaction with retinoic acid or its reactive form. The use of this non-selective activated form allows for the obtainment of final esterification products characterised by the fact that the hydroxyl groups of the monosaccharidic units of the polysaccharide that have been esterified with retinoic acid are both the primary and the secondary hydroxyl groups.

The preferred activation procedure according to the invention is the selective activation of the primary hydroxyl groups. The preferred activation process for carrying out the selective activation is the substitution of the hydroxyl groups with halogen atoms by means of selective halogenation reaction which entails the following steps: suspension of the polysaccharide in organic solvent under stirring for 1–5 hours at 25–100° C., addition of an halogenating agent at a temperature that can vary from −20° C. to 100° C. under constant stirring for 1–20 hours and possible alkalynisation of the reaction mixture at a pH ranging from 9 to 11. At the end of the reaction, the mixture is neutralized and the activated polysaccharide is recovered according to conventional procedures.

The halogenating agent is selected in the group consisting of methanesulphonyl bromide, methanesulphonyl chloride, p-toluenesulphonyl bromide, p-toluenesulphonyl chloride, thionyl chloride, thionyl bromide; as an alternative it is possible to use oxalyl bromide, oxalyl chloride, phosgene, bis-trichloromethylcarbonate and mixtures thereof. The preferred agents are selected in the group consisting of methanesulphonyl bromide, or methanesulphonyl chloride. The solvents that can be used are the aprotic solvents such as dialkylsulphoxide, dialkylcarboxamides, specifically C1–C6-dialkylsulphoxides, such as for example dimethylsulphoxide, C1–C6-dialkylamides of C1–C6 aliphatic acids, such as for example N,N-dimethylformamide, N,N-diethylformamide, N,N-dimethylacetamide, N,N-diethylacetamide. The preferred solvents are N,N-dimethylformamide, dimethylsulphoxide, N-methylpyrrolidone.

When the polysaccharide that is activated is anionic, both its free acid form and its salified form or the esterified form of the carboxyl can be used. The salified form is the preferred one. Further details on the activation process by halogenation are referred to in WO99/18133.

The use of this polysaccharide in its selectively activated form as described above allows for the obtainment of the final esterified products characterised by the fact that the hydroxyl groups of the monosaccharidic units of the polysaccharide esterified with retinoic acid are the primary hydroxyl groups.

Any other reactions selectively allowing the activation of the primary hydroxyl groups by their replacement with a good leaving group can in principle be applied for the preparation of the esters of the invention. As an example C6 O-alkylsulphonates or C6 O-arylsulphonate of polysaccharides can be produced by treating the polysaccharide in organic solvent with the required amount of reagent and catalyst at low temperature (eg. below room temperature).

The formation step of the ester linkage between the acid group of retinoic acid or one of its reactive form and the hydroxyl groups of the monosaccharidic units of the polysaccharide in activated form occurs by addition of the polysaccharide solution to the solution of retinoic acid under mechanical stirring. The reaction is carried out for 5–20 hours and the product is recovered according to conventional procedures. The preferred procedure entails the precipitation of the product from the solution, the recovery of the solid product, the elimination of the solvent, the drying of the product.

In a first preferred embodiment of this invention a reactive form of retinoic acid is reacted with the polysaccharide having the hydroxyl groups in activated form. More specifically the acyl halide of retinoic acid is reacted with the alcoholated hydroxyl groups of the polysaccharide.

In a second preferred embodiment the retinoic acid as such is reacted with the polysaccharide having activated primary hydroxyl groups. More specifically the retinoic acid as such is reacted with the selectively halogenated polysaccharide.

The polysaccharidic esters of retinoic acid described in the invention can be used both in the pharmaceutical and cosmetic field. The polysaccharidic ester of retinoic acid described in the invention allows to overcome the drawbacks of retinoic acid, mainly those due to the high toxicity and instability of the active compound. It is in fact known that retinoic acid and retinoids used at therapeutical doses in topical applications cause skin irritations that markedly hamper and limit the therapeutical treatment. The lipophylic character of this active compound makes the preparation of pharmaceutical formulations difficult, specifically those devised for usage different from the topical one. These new polysaccharidic derivatives containing retinoic acid show higher stability and minor toxicity than the active compound as such and are suitable for the preparation of different types of formulations. Said derivatives can therefore be used in the preparation of medicaments, since they allow for an improvement of several histological parameters, such as for example the epidermis thickening including the "stratum granulosum", an increased thickness of the "rete ridges" and the number of papillae in the derma, a gradual replacement of age-related accumulation of elastin by collagen and peptidoglycans, a normalization of the melanocytes function, and an increase in the number of fibroblasts. The compounds are therefore particularly useful in dermatology, in the treatment of skin pathologies, among which for example psoriasis, and in the treatment of pathologies due to skin ageing. Moreover, it has been observed that the compounds of the invention induce tumour cell differentiation. Therefore, they offer one potential alternative to conventional cytotoxic treatments. They are therefore of interest in the treatment of precancerous epithelial lesions and of tumours, among which specifically epithelial tumours such as tumours of the breast, cervix, prostate, bladder, colon, oesophagus, stomach, larynx, and oral cavity. The compounds turn out to be interesting for their use in the treatment of ophtalmologic, cardiovascular, inflammatory, neurodegenerative, and lung diseases.

One further object of this invention are the pharmaceutical compositions containing as an active compound the polysaccharidic esters of the invention.

One further object of this invention consists in cosmetic compositions containing the polysaccharidic esters.

The pharmaceutical compositions are suitable for systemic and topical administration. The cosmetic compositions are suitable for topical administration. When they are in a liquid form, the compositions can be in the form of solutions or suspension, both in an aqueous or non aqueous medium. Alternatively, the compositions can be formulated in a solid form, wherein the freeze-dried or dried product is dissolved or suspended by addition of a suitable liquid solvent immediately before administration. The compositions in solid or semisolid forms are inserts, gel, creams, ointments, foams, granulates, powders, tablets, pills, capsules or microencapsulated formulations. Other kinds of compositions can be set up by techniques known to the experts.

In order to illustrate the invention, the following examples are given.

EXPERIMENTAL PART

Example 1

Method for the Determination of the Weight Average Molecular Weight (MW) of Hyaluronan The weight average molecular weight is determined by HP-SEC (High Performance Size Exclusion Chromatography). The analysis conditions are as follows: Chromatograph: HPLC Jasco PU-880 with Rheodyne 9125 injector. Columns: TSK PW×1 G6000+G5000+G3000 (TosoHaas) 300 mm×7.8 mm ID, 13, 10, 6 μm particle size; Temperature 40° C. Mobile phase: NaCl 0.15 M. Flow: 0.8 ml/min. Detector: LALLS CMX-100 (TSP Chromatix), Po=300–400 mV; differential refraction index: 410 (Waters), Sensitivity 128×; Temperature 32° C. Injected volume: 100 μl. The products are solubilised in 0.15 M NaCl at a concentration of about 1.0 mg/ml and are kept under stirring for 12 hours. The solutions are filtered through a 0.45 μm (Millipore) and then injected into the chromatograph. The analysis allows the determination of MW (weight average molecular weight), Mn (number average molecular weight), and PI (polydispersity). The concentrations of the polysaccharidic solutions are checked by the integral of the refractive index. Tetrabutylammonium hyaluronan is analysed after ion exchange between tetrabutylammonium and sodium, the determination of its MW is therefore made on the corresponding sodium salt.

Example 2

Hyaluronan Ester with Trans-Retinoic Acid 2.1 Preparation of Hyaluronan Having the Hydroxyl Groups Activated.

250 mg of tetrabutylammonium hyaluronan (the sodium salt thereof has MW: 100000) are placed in a round-bottom flask 1.1 mL of a 40% tetrabutylammonium solution are added, under magnetic stirring at room temperature up to complete solubilization. The solution is then frozen and freeze-dried.

2.2 Preparation of the Reactive Form of Retinoic Acid.

605 mg of all-trans-retinoic acid are solubilised in 5 mL of anhydrous N,N-dimethylformamide in a three-necked flask, under magnetic stirring at room temperature, under nitrogen flux sheltered from light. Separately, in a three-necked flask, 3 mL of ethyl ether are poured, 300 μl of anhydrous N,N-dimethylformamide and 208 μl of oxalyl chloride, under magnetic stirring at room temperature under nitrogen flux for 15 minutes. The solution of retinoic acid in N,N-dimethylformamide is dropped onto the solid obtained in this way. The system is kept under magnetic stirring, under nitrogen flux, and sheltered from light for 1 hour.

2.3 Preparation of the Ester.

In a round-bottom flask the polysaccharidic sample prepared (2.1) is solubilised in 10 mL of N,N-dimethylformamide at room temperature, under magnetic stirring for 4 hours. The solution obtained in this way is added by a dropping funnel to the solution of retinoic acid prepared (2.2) with a 2 mL/minute flow rate. The reaction mixture is kept at room temperature under magnetic stirring, under nitrogen flux and sheltered from light for 16 hours. After that, the solution is concentrated at reduced pressure and the product precipitated with 5 volumes of acetone is recovered by filtration, washed several times and finally dried. 90 mg of products are obtained. The product was characterised by nuclear magnetic resonance spectroscopy ($^1$H-NMR). The spectrum shows the signals due to the protons of the polysaccharides and to all the protons of retinoic acid. From evaluation of the chemical shifts related to the signals due to retinoic acid, retinoic acid is confirmed to keep its all-trans isomeric form. From comparison of the UV absorption spectra at its absorbance maximum at 355 nm of a standard solution of retinoic acid with that of a solution at known concentration of the product the degree of substitution is determined to be 0.2.

Example 3

Hyaluronan Ester with Trans-Retinoic Acid 3.1 Preparation of Hyaluronan Having the Hydroxyl Groups Activated.

250 mg of tetrabutylammonium hyaluronan (the sodium salt thereof has MW: 100000) are poured in a round-bottom flask. 300 μl of a tetrabutylammonium solution and 400 μl of N,N-dimethylformamide are added and the mixture is kept under magnetic stirring at room temperature, up to complete solubilization. The solution is then frozen and freeze-dried.

3.2 Preparation of the Reactive Form of Retinoic Acid.

242 mg of retinoic acid are solubilised in 2 mL of anhydrous N,N-dimethylformamide in a three-necked flask, under magnetic stirring at room temperature, under nitrogen flux and sheltered from light for 3 hours. Separately, in a three-necked flask, 2 mL of ethyl ether, 100 μl of anhydrous N,N-dimethylformamide and 83 μl of oxalyl chloride are added. The mixture is kept under magnetic stirring at room temperature under nitrogen flux for 15 minutes. A solution of retinoic acid in N,N-dimethylformamide is dropped onto the solid obtained in this way. The system is kept under magnetic stirring, under nitrogen flux and sheltered from light for 1 hour.

3.3 Preparation of the Ester

In a round-bottom flask, the polysaccharidic sample (3.1) is solubilised in 14 mL of N,N-dimethylformamide at room temperature under magnetic stifling for 4 hours. The solution obtained in this way is added by a dropping funnel to the solution of retinoic acid (3.2) at a flow rate of 2 mL/minute. The reaction mixture is kept at room temperature under magnetic stirring, under nitrogen flux and sheltered from light for 16 hours. After that, the solution is concentrated, the product is then precipitated with 5 volumes of acetone, hence recovered by filtration, washed several times and finally dried. 10 mg of products are obtained. The product has been characterised as described in Example 2. The degree of substitution is 0.05.

Example 4

Ester of Hyaluronan with Trans-Retinoic Acid 4.1 Preparation of Hyaluronan Having the Hydroxyl Groups Activated.

250 mg of tetrabutylammonium hyaluronan (the sodium salt thereof has MW: 100000) are poured into a round-bottom flask, 500 μl of a solution of tetrabutylammonium are added and the mixture is kept under magnetic stirring up to complete solubilisation. The solution is then frozen and freeze-dried.

4.2 Preparation of the Reactive Form of Retinoic Acid.

121 mg of retinoic acid are solubilised in 3 mL of anhydrous N,N-dimethylformamide in a three-necked flask under magnetic stirring at room temperature, under nitrogen flux, and sheltered from light for 4 hours. Separately, 2 mL of ethyl ether, 100 μl of anhydrous N,N-dimethylformamide and 83 μl of oxalyl chloride in a three-necked flask are added. The mixture is kept under magnetic stirring at room temperature under nitrogen flux for 15 minutes. The solution of retinoic acid in N,N-dimethylformamide is dropped onto the solid obtained in this way. The system is kept under magnetic stirring, under nitrogen flux and sheltered from light for 1 hour.

4.3 Preparation of the Ester.

In a round bottom flask, the polysaccharide (4.1) is solubilised in 10 mL of N,N-dimethylformamide at room temperature, under magnetic stirring for 3 hours. The solution obtained in this way is added by a dropping funnel to the solution of retinoic acid (4.2) at a flow rate of 2 mL/minute. The reaction mixture is kept at room temperature under magnetic stirring, under nitrogen flux and sheltered from light for 16 hours. After concentration of the solution, the product is then precipitated in 5 volumes of acetone, recovered by filtration, washed several times and finally dried. 150 mg of product are obtained. The product was characterised as described in Example 2. The degree of substitution is 0.06.

Example 5

Hyaluronan Ester with Trans-Retinoic Acid 5.1 Preparation of Hyaluronan Having the Hydroxyl Groups Activated.

260 mg of tetrabutylammonium hyaluronan (the sodium salt thereof has MW: 100000) are poured into a round-bottom flask, 1.2 mL of 40% tetrabutylammonium solution are added and the mixture is kept under magnetic stirring up to complete dissolution. The solution is then frozen and freeze-dried.

5.2 Preparation of the Reactive Form of Retinoic Acid 126 mg of retinoic acid are solubilised in 3 mL of anhydrous N,N-dimethylformamide in a three-necked flask under magnetic stirring at room temperature and sheltered from light for 4 hours. Separately, 2 mL of ethyl ether are poured into a three necked flask, and 50 μl of anhydrous N,N-dimethylformamide and 43 μl of oxalyl chloride are added. The mixture is kept under magnetic stirring at room temperature under nitrogen flux for 15 minutes. The solution of retinoic acid in N,N-dimethylformamide obtained in this way is dropped onto the solid. The system is kept under magnetic stirring, under nitrogen flux and sheltered from light for 1 hour.

5.3 Preparation of the Ester.

In a round bottom flask, the polysaccharide (5.1) is solubilised in 10 mL of N,N-dimethylformamide at room temperature under magnetic stirring for 4 hours. The solution obtained in this way is added by a dropping funnel to the solution of retinoic acid (5.2) at a flow rate of 2 mL/minute. The reaction mixture is left at room temperature under magnetic stirring, under nitrogen flux and sheltered from light for 16 hours. After that, the solution is concentrated and the product is precipitated in 5 volumes of acetone and recovered by filtration, washed several times and finally dried. 80 mg of product are obtained. The product is then characterised as in Example 2. The degree of substitution is 0.03.

Example 6

Ester of Hyaluronan with Trans-Retinoic Acid 6.1 Preparation of Hyaluronan Having the Primary Hydroxyl Groups Activated.

15 ml of anhydrous N,N-dimethylformamide are heated at 80° C. in a three-necked flask under magnetic stirring and under nitrogen flux. 340 mg of tetrabutylammonium hyaluronan (the sodium salt thereof has MW: 100000) are added and the system is kept under stirring up to complete solubilisation. The solution obtained in this way is cooled down to room temperature and then to 0° C., 870 mg of methanesulphonyl bromide are added. The reaction mixture is left under stirring for 20 minutes and then heated to 80° C. for 16 hours. The system is then cooled down to room temperature and the reaction is blocked by addition of 10 mL of MilliQ water. The system is then neutralised with a base, concentrated at reduced pressure to one third of its volume and precipitated in 100 ml acetone. The sample is then recovered by filtration, washed with acetone, and dispersed in 20 mL of MilliQ water at pH 10. It is neutralised with HCl and dialysed against MilliQ water. 210 mg of product are obtained. The product is characterised by nuclear magnetic resonance spectroscopy ($^{13}$C-NMR) that has revealed the halogenation of the primary hydroxyl group (ppm 34.5) and has allowed the calculation of the bromination degree that is 90%.

6.2 Preparation of the Ester.

100 mg of bromo hyaluronan (6.1) are dispersed in 8 ml of N,N-dimethylformamide at 80° C. in a three-necked flask. Three hours after, the system is cooled down to room temperature and 250 mg of retinoic acid dissolved in 2 mL of N,N-dimethylformamide are added. The reaction mixture is kept at room temperature, in the presence of a base under nitrogen flux and sheltered from light for 48 hours.

The system is then concentrated, the product precipitated in 50 mL of acetone, recovered by filtration, washed several times and finally dried. 70 mg of product are obtained. The product is then characterised by nuclear magnetic resonance spectroscopy ($^1$H-NMR) that has revealed the presence of signals that can be referred to retinoic acid. From evaluation of the chemical shifts related to retinoic acid, retinoic acid is confirmed to keep its all-trans isomeric form. The degree of substitution, determined as described in Example 2, ranges from $10^{-2}$ and $10^{-6}$.

Example 7

Butyric and Retinoic Mixed Ester of Hyaluronan 7.1 Preparation of Hyaluronan Having the Hydroxyl Groups Activated.

250 mg of tetrabutylammonium hyaluronan (the sodium salt thereof has MW: 100000) are poured into a round-bottom flask, 1.1 mL of a 40% tetrabutylammonium solution are added and kept under magnetic stirring at room temperature up to complete solubilisation. The solution is then frozen and freeze-dried.

7.2 Preparation of Hyaluronan Esterified with Butyric Acid.

The polysaccharide prepared (7.1) is solubilised in 10 mL of anhydrous N,N-dimethylformamide in a round-bottom flask, at room temperature under magnetic stirring. The solution obtained in this way is added, by a dropping funnel, to a solution of 16 μL of butyric anhydride and 2 mL of N,N-dimethylformamide.

The reaction mixture is kept at room temperature under magnetic stirring and under nitrogen flux for 2.5 hours.

7.3 Preparation of the Reactive Form of Retinoic Acid.

4 mL of ethyl ether, 75 μL of anhydrous N,N-dimethylformamide and 83 μL of oxalyl chloride are poured into a three-necked flask, supplied with magnetic stirring. The mixture is kept under under magnetic stirring at room temperature for 15 minutes and under nitrogen flux to remove the ethyl ether. A solution of 242 mg of retinoic acid in 4 mL of anhydrous N,N-dimethylformamide is added by magnetic stirring, under nitrogen flux, and sheltered from light for 1 hour.

7.4 Preparation of the Ester.

In a three-necked flask, the solution of retinoic acid (7.3) is added by a dropping funnel to the polysaccharidic solution (7.2) at a flow rate of 2 mL/minute. The reaction mixture is kept at room temperature under magnetic stirring, under nitrogen flux and sheltered from light for 16 hours. After that, the solution is concentrated, the product precipitated and recovered by filtration, washed several times and hence dried. 100 mg of product are obtained. The product is then characterised by nuclear magnetic resonance spectroscopy ($^1$H-NMR) that have revealed the presence of signals that can be referred to residues of retinoic acid as described in Example 6. The signals that confirm the presence of butyric acid (0.90, 1.62, 2.39 ppm) are detected; they allow the determination of the butyration degree that is 0.24. The degree of substitution is determined as in Example 2 is 0.06.

Example 8

Ester of Scleroglucan with Trans-Retinoic Acid 8.1 Preparation of Scleroglucan Having the Hydroxyl Groups Activated.

150 mg of scleroglucan (weight average molecular weight: Mw: 2400000) are poured into a round-bottom flask, 980 μL of a tetrabutylammonium solution are added and the mixture is kept under magnetic stirring up to complete solubilisation. The solution is then frozen and freeze-dried.

8.2 Preparation of the Reactive Form of Retinoic Acid.

280 mg of retinoic acid are poured into a three-necked flask supplied with magnetic stirring. 4 ml of dimethylsulphoxide are added and kept under magnetic stirring, at 50° C. and under nitrogen flux for 2 hours. To the solution obtained in this way, 450 mg of N,N-dimethylaminopyridine and 380 mg of dicyclohexylcarbodiimide are added by magnetic stirring under nitrogen flux and sheltered from light for 4 hours and 35 minutes.

8.3 Preparation of the Ester.

In a round bottom flask, the polysaccharide (8.1) is solubilised in 8 mL of anhydrous dimethylsulphoxide at room temperature under magnetic stirring. The solution obtained in this way is added, by dropping funnel, to the solution of retinoic acid (8.2) at a 2 mL/minute flow rate. The reaction mixture is kept at room temperature under magnetic stirring, under nitrogen flux and sheltered from light for 19 hours. The product is then recovered by washing the reaction system with 50 mL of ethyl ether for three times, the precipitate is washed, recovered by filtration, washed several times and finally dried. 160 mg of product are obtained. The product is characterised by nuclear magnetic resonance spectroscopy ($^1$H-NMR) that has revealed the presence of retinoic acid bound to the polysaccharide as described in Example 6.

Example 9

Ester of Scleroglucan with Trans-Retinoic Acid 9.1 Preparation of Scleroglucan Having the Primary Hydroxyl Groups Activated.

In a three-necked flask, 120 mL of anhydrous N,N-dimethylformamide under magnetic stirring and under nitrogen flux are heated up to 80° C. 600 mg of scleroglucan (weight average molecular weight: 280000) are added and the system is kept under stirring for 4 hours. The system obtained in this way is cooled down first to room temperature and then to 0° C.; 2.94 g of methanesulphonyl bromide are added. The mixture is kept under stirring for further 20 minutes and then heated to 80° C. for 16 hours. The mixture is cooled down to room temperature and the reaction is blocked by adding 30 mL of MilliQ water. The system is then neutralised with NaOH, concentrated and the product is then precipitated in 300 ml of acetone and recovered by filtration. The product is then precipitated in 300 ml of acetone and recovered by filtration. The product is dispersed in 150 mL of MilliQ water, some base is added and heated to 50° C. under magnetic stirring up to complete solubilisation; it is finally neutralised with HCl and dialysed against MilliQ water. The sample is recovered by freeze-drying. 570 mg of product are obtained. The product is characterised by nuclear magnetic resonance spectroscopy ($^{13}$C-NMR) that has revealed a bromination degree of 55%, as described in Example 6.

9.2 Preparation of the Ester.

200 mg of bromo scleroglucan (9.1) are dissolved in 15 mL of dimethylsulphoxide in a three-necked flask, at 80° C. under magnetic stirring and under nitrogen flux. After 3 hours, the solution obtained in this way is cooled down to room temperature and 370 mg of retinoic acid dissolved in 5 mL of dimethylsulphoxide are added to it in the presence of a base. The reaction mixture is left at room temperature, under nitrogen flux and sheltered from light for 48 hours. Then the system is precipitated in 100 mL of acetone and the sample is recovered by filtration, washed several times and finally dried 60 mg of product are obtained. The product is characterised by nuclear magnetic resonance spectroscopy ($^{1}$H-NMR) that has revealed the presence of signals that can be referred to retinoic acid as described in Example 6. The degree of substitution, determined as described in Example 2, ranges from $10^{-2}$ to $10^{-6}$.

Example 10

Induction of Cardiac Differentiation of Embryonal Pluripotent Murine Teratocarcinoma Cells by the Polysaccharidic Esters of Example 3, 4, 5

The experiments were carried out on P19 cells, embryonal pluripotent murine teratocarcinoma cell line (European Collection of Cell Cultures, UK). These cultured cells indifferentiately proliferate but can be transformed into several cell phenotypes in the presence of differentiating agents, thus selectively summarising the first molecular events that take place during the embryonal growth. Specifically, in the presence of dimethylsulphoxide (DMSO), P19 cells turn into myocardial cells supplied with spontaneous contractile activity, whereas they turn into neuronal cells in the presence of retinoic acid (McBurney M. W., et al., Nature 299: 165–167, 1982). P19 cells are cultivated in a suspension in alpha-mem medium in 60 mm Petri dishes, either in the absence or in the presence of the hyaluronan esters of the invention. After 4 days of treatment, the total RNA was extracted according to the procedure described by Chomczynsky and Sacchi (Chomczynsky, P., N. Sacchi, Anal. Biochem. 162: 156–159, 1987) and the expression of specific transcripts was evaluated by RT-PCR and RNase protection. The P19 indifferentiated cells exposure to the esters prepared according to Examples 3, 4, 5 has produced a marked increase of the prodynorphin gene expression, which is an inducer of cardiomyogenesis in pluripotent cells (Ventura C., Maioli M., Circ. Res. 87: 189–194, 2000), followed by the gene induction of the GATA-4 and Nkx-2.5 genes codifying for tissue-specific transcription factors that are responsible for the cardiogenesis process in several animal species from Drosophila to mouse up to man (Crepin C. et al, Mol. Cell. Biol. 15: 4095–4102, 1995; Skeijanc, I. et al., J. Biol. Chem. 273: 34904–34910, 1998). The quantitative analysis of the mRNA levels by RT-PCR and RNase protection has outlined that, after exposure of the P19 cells to the hyaluronan esters, not only the prodynorphin gene and the GATA-4 and Nkx-2.5 cardiogenetic genes are expressed, but also the alphamyosin heavy chain and myosin light chain-2V transcripts, that during embryogenesis, are markers of myocardial differentiation (Ventura C., Maioli M.; Circ. Res. 87: 189–194, 2000). The analysis of the transcription rate of the GATA-4 and Nkx-2.5 genes and of the prodynorphin gene carried out in isolated nuclei by nuclear run-off transcription techniques (Ventura C., et al, J. Biol. Chem. 270: 30115–30120, 1995) has evidenced that the response triggered by the compounds of the invention had occurred at the gene transcriptional level, thus excluding a mere effect at the messenger stability level. These results show that a gene expression programme responsible for cardiac differentiation of embryonal pluripotent carcinoma cells can be induced without approaches of "gene delivery". Moreover, the data show how the differentiating effect exerted on the P19 cells can be reconverted from normal evolution in a neurogenetic sense to the induction of a myocardial architecture.

What is claimed is:

1. Polysaccharidic ester of retinoic acid, wherein the hydroxyl groups of the monosaccharidic units of the polysaccharide are partially or totally esterified with retinoic acid.

2. The ester according to claim 1, wherein the hydroxyl groups of the monosaccharidic units of the polysaccharide are partially esterified with retinoic acid.

3. The ester according to claim 1, wherein the hydroxyl groups of the monosaccharidic units of the polysaccharide esterified with retinoic acid are the primary hydroxyl groups.

4. The ester according to claim 1, wherein the hydroxyl groups that are not involved in the esterification with retinoic acid are esterified with acids having a C1–C5 alkyl chain.

5. The ester according to claim 4, wherein the acid having a C1–C5 alkyl chain is butanoic acid.

6. The ester according to claim 1, wherein retinoic acid is selected from the group consisting of all-trans-retinoic, 9-cis-7,11,13-tri-trans-retinoic acid and 13-cis-7,9,11-trans-retinoic acid.

7. The polysaccharidic ester according to claim 1, wherein the polysaccharide is neutral or anionic.

8. The polysaccharidic ester according to claim 1, wherein the polysaccharide is linear or branched and is constituted of glucosidic units selected from the group consisting of D-glucose, D-xylose, D-arabinose, D- and L-mannose, D-galactose, L-fucose, L-rhamnose, D-galacturonic acid, D-glucuronic acid, D-mannuronic acid, D-guluronic acid, L-iduronic acid and D-fructose.

9. The polysaccharidic ester according to claim 1, wherein its monosaccharidic units are bound by β-(1→3), β-(1→4), α-(1→3), α-(1→4), α-(1→6), β-(1→2).

10. The polysaccharidic ester according to claim 7, wherein said polysaccharide is a β-D-glucan.

11. The polysaccharidic ester according to claim 7, wherein said polysaccharide is selected from the group consisting of scleroglucan, lentinan, schizophyllan, pachimaran, curdlan and laminaran.

12. The polysaccharidic ester according to claim 7, wherein said polysaccharide is hyaluronan or a salt thereof.

13. The polysaccharidic ester according to claim 7, wherein said polysaccharide is a sulphated polysaccharide.

14. Process for the preparation of the polysaccharidic esters described in claim 1 comprising the formation of ester bonds between the acid group of the retinoic acid and the hydroxyl groups of the monosaccharidic units of the polysaccharide in a suitable organic solvent or mixtures of organic solvents.

15. The process according to claim 14, wherein the formation of said ester bond occurs by means of an esterification reaction between the acid group of the retinoic acid in the from of an acyl halide and the hydroxyl groups of polysaccharide in the alcoholated form.

16. The process according to claim 14, wherein the formation of said ester bond occurs by means of an esterification reaction between the acid group of the retinoic acid and the primary hydroxyl groups of the monosaccharidic units of the polysaccharide wherein said primary hydroxyl groups have been activated by selective halogenation of the polysaccharide.

17. Therapeutic method for the treatment of a pathology selected from the group consisting of skin pathologies, pathologies due to skin aging, epithelial tumors and opthalmological, cardiovascular, inflammatory, neurodegenerative and lung diseases comprising administering to an individual afflicted with said pathology a therapeutically effective amount of a polysaccharidic ester according to claim 1.

18. Pharmaceutical composition wherein the active compound is a polysaccharidic ester described in claim 1 in a mixture with one or more suitable excipient.

19. Cosmetic composition containing the polysaccharidic ester according to claim 1 in a mixture with one or more suitable excipients.

* * * * *

UNITED STATES PATENT AND TRADEMARK OFFICE
CERTIFICATE OF CORRECTION

PATENT NO. : 6,897,203 B2
DATED : May 24, 2005
INVENTOR(S) : Allessandro Rastrelli et al.

It is certified that error appears in the above-identified patent and that said Letters Patent is hereby corrected as shown below:

Column 12,
Lines 47 and 48, "trans" and "cis" should be italicized (all occurrences).

Column 13,
Line 6, change "esters" to -- ester --.
Line 14, change "from" to -- form --.

Column 14,
Line 14, change "excipient" to -- excipients --.

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO.    : 6,897,203 B2
DATED         : May 24, 2005
INVENTOR(S)   : Alessandro Rastrelli et al.

It is certified that error appears in the above-identified patent and that said Letters Patent is hereby corrected as shown below:

Title page,
Item [22], PCT Filed:
Change "Jan. 16, 2002" to -- July 16, 2002 --.

Signed and Sealed this

Fifteenth Day of November, 2005

JON W. DUDAS
*Director of the United States Patent and Trademark Office*